(12) United States Patent
Woelfert et al.

(10) Patent No.: US 7,994,361 B2
(45) Date of Patent: Aug. 9, 2011

(54) MODERATE-PRESSURE GAS PHASE PHOSGENATION

(75) Inventors: Andreas Woelfert, Bad Rappenau (DE); Christian Mueller, Mannheim (DE); Eckhard Stroefer, Mannheim (DE); Markus Weber, Ludwigshafen (DE); Joachim Pfeffinger, Ludwigshafen (DE); Carsten Knoesche, Niederkirchen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1705 days.

(21) Appl. No.: 10/523,919

(22) PCT Filed: Jul. 24, 2003

(86) PCT No.: PCT/EP03/08108
§ 371 (c)(1), (2), (4) Date: Feb. 7, 2005

(87) PCT Pub. No.: WO2004/026813
PCT Pub. Date: Apr. 1, 2004

(65) Prior Publication Data
US 2005/0272910 A1    Dec. 8, 2005

(30) Foreign Application Priority Data

Aug. 20, 2002  (DE) .................................. 102 38 995

(51) Int. Cl.
*C07C 249/00* (2006.01)
(52) U.S. Cl. ...................................................... 560/330
(58) Field of Classification Search .................... None
See application file for complete search history.

(56) References Cited

U.S. PATENT DOCUMENTS 4,581,174 A * 4/1986 Ohlinger et al. .............. 560/347
5,449,818 A * 9/1995 Biskup et al. ................. 560/347

FOREIGN PATENT DOCUMENTS

| DE | 21 12 181 | 10/1972 |
| EP | 0 150 435 | 8/1985 |
| EP | 0 570 799 | 11/1993 |
| EP | 0 593 334 | 4/1994 |
| EP | 0 699 657 | 3/1996 |
| WO | 99 40059 | 8/1999 |

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

The invention relates to a process for preparing aromatic diisocyanates by reaction of phosgene with diamines in the gas phase, in which the reaction is carried out in a reaction zone at moderate pressures, i.e. the pressure in this reaction zone is more than 3 bar and less than 20 bar.

13 Claims, 1 Drawing Sheet

MODERATE-PRESSURE GAS PHASE PHOSGENATION

CROSS REFERENCES TO RELATED APPLICATIONS

This application is a national stage application of International Patent Application No. PCT/EP03/08108, filed on Jul. 24, 2003, and claims priority to German Patent Application No. 102 38 995.0, filed on Aug. 20, 2002, both of which are incorporated herein by reference in their entireties.

The present invention relates to a process for preparing aromatic diisocyanates by reaction of phosgene with diamines in the gas phase, in which the reaction is carried out in a reaction zone at moderate pressures, i.e. the pressure in this reaction zone is more than 3 bar and less than 20 bar.

The preparation of organic isocyanates from the corresponding amines by phosgenation in the gas phase is generally known. While the phosgenation of aliphatic amines in the gas phase has been adequately described, the industrial phosgenation of aromatic amines in the gas phase has not yet been realized. In particular, it suffers from problems caused by formation of solids which block the mixing and reaction apparatuses and reduce the yield. In addition, it is known that the reactivity of aromatic amines with phosgene is lower because of the aromatic ring structure, which leads to poorer space-time yields.

A number of possible ways of reducing these problems have been proposed. EP-A-570 799 describes a continuous gas-phase phosgenation of aromatic amines in which the reaction is carried out at temperatures above the boiling point of the diamine used and the mixing of the reactants is carried out in such a way that the mean contact time is from 0.5 to 5 seconds and a deviation of less than 6% from the mean contact time is achieved.

EP-A-593 334 describes a process for preparing aromatic isocyanates in the gas phase using a tube reactor in which mixing of the starting materials is achieved without mechanical stirring by means of a constriction in the walls.

EP-A-699 657 discloses a process for preparing aromatic diisocyanates in the gas phase in a mixing reactor which is divided into two zones of which the first ensures complete mixing of the starting materials and the second ensures plug flow.

It is an object of the invention to provide a process which ensures an industrially advantageous reaction, in particular in respect of a high space-time yield and a low occurrence of interfering solids, of aromatic diamines with phosgene in the gas phase to form the corresponding diisocyanates.

A further object of the invention is to provide a production plant by means of which the process of the present invention can be carried out advantageously and which contains very little of the toxic substance phosgene.

We have found that this object is achieved by carrying out the gas-phase phosgenation at moderate pressures.

The present invention accordingly provides a process for preparing aromatic diisocyanates by reaction of phosgene with diamines in the gas phase, wherein the reaction is carried out in a reaction zone in which the pressure is more than 3 bar and less than 20 bar.

The invention also provides a production plant for preparing aromatic diisocyanates by reaction of phosgene with diamines in the gas phase at a pressure of more than 3 bar and less than 25 bar which has a ratio of production capacity to phosgene holdup of more than 3200 [metric tons of diisocyanate per year/kilogram of phosgene].

In the process of the present invention, it is possible to use any primary aromatic diamine which can be brought into the gas phase preferably without decomposition, or a mixture of two or more such amines. Preference is given, for example, to methylenedi(phenylamine) (individual isomers and/or an isomer mixture), toluenediamine, R,S-1-phenylethylamine, 1-methyl-3-phenylpropylamine, 2,6-xylidine, naphthalenediamine and bis(3-aminophenyl) sulfone. The process can be employed particularly advantageously for preparing methylenedi(phenyl isocyanate) (MDI) and tolylene diisocyanate (TDI), in particular for tolylene diisocyanate. The invention does not encompass the gas-phase phosgenation of aliphatic diamines.

An additional inert medium can be employed in the process of the present invention. The inert medium is a medium which at the reaction temperature is present as a gas in the reaction zone and does not react with the starting materials. The inert medium is generally mixed with amine and/or phosgene prior to the reaction. For example, it is possible to use nitrogen, noble gases such as helium or argon or aromatics such as chlorobenzene, dichlorobenzene or xylene. Preference is given to using nitrogen as inert medium. Particular preference is given to monochlorobenzene.

In general, the inert medium is used in such an amount that the molar ratio of inert medium to diamine is from >2 to 30, preferably from 2.5 to 15. The inert medium is preferably introduced into the reaction zone together with the diamine.

A solvent can be used in the process of the present invention. In contrast to the inert medium, the solvent is generally introduced only after the reaction of the starting materials in the reaction zone, i.e. preferably in the work-up stage. The solvent is preferably present in liquid form. Suitable solvents are substances which are inert toward the starting materials and products of the process of the present invention. The solvent should preferably have good, i.e. selective, solvent properties for the isocyanate to be prepared.

In a preferred embodiment, the inert medium and the solvent are the same compound, in which case particular preference is given to using monochlorobenzene.

The reaction of phosgene with diamine occurs in a reaction zone which is generally located in a reactor, i.e. the term reaction zone refers to the region or space in which the reaction of the starting materials occurs, while the term reactor refers to the apparatus in which the reaction zone is present. For the present purposes, the reaction zone can be any customary reaction zone known from the prior art which is suitable for noncatalytic, single-phase gas reactions, preferably for continuous noncatalytic, single-phase gas reactions, and will withstand the moderate pressures required. Materials suitable for contact with the reaction mixture are, for example, metals such as steel, tantalum, silver or copper, glass, ceramic, enamels or homogeneous or heterogeneous mixtures thereof. Preference is given to using steel reactors. The walls of the reactor can be smooth or profiled. Suitable profiles are, for example, grooves or corrugations.

It is generally possible to use the types of reactor construction known from the prior art. Preference is given to using tube reactors.

It is likewise possible to use essentially cuboidal reaction zones, preferably plate reactors or plate reaction zones. A particularly preferred plate reactor has a ratio of width to height of at least 2:1, preferably at least 3:1, particularly preferably at least 5:1 and in particular at least 10:1. The upper limit for the ratio of width to height depends on the desired capacity of the reaction zone and is not restricted in principle. Reaction zones having a ratio of width to height up to 5000:1, preferably 1000:1, have been found to be industrially practicable.

In the process of the present invention, the mixing of the reactants occurs in a mixing device which produces high shear in the reaction stream fed into the mixing device. As mixing device, preference is given to a static mixer or a mixing nozzle which is installed upstream of the reactor. Particular preference is given to using a mixing nozzle.

The reaction of phosgene with diamine in the reaction zone is carried out at absolute pressures of from >3 bar to <20 bar, preferably from 3.5 bar to 15 bar, particularly preferably from 4 bar to 12 bar, in particular from 5 to 12 bar.

The pressure in the feed lines to the mixing device is generally higher than the pressure indicated above in the reactor. This pressure depends on the choice of mixing device. The pressure in the feed lines is preferably from 20 to 1000 mbar, particularly preferably from 30 to 200 mbar, higher than that in the reaction zone.

The pressure in the work-up apparatus is generally lower than that in the reaction zone. The pressure is preferably from 50 to 500 mbar, particularly preferably from 80 to 150 mbar, lower than that in the reaction zone.

In the process of the present invention, the reaction of phosgene with diamine occurs in the gas phase. For the purposes of the present invention, the term "reaction in the gas" phase means that the feed streams react with one another in the gaseous state.

In the process of the present invention, the temperature in the reaction zone is selected so that it is below the boiling point of the diamine used under the pressure conditions prevailing in the reaction zone. Depending on the amine used and the pressure which has been set, the temperature in the reaction zone is advantageously from >200° C. to <600° C., preferably from 280° C. to 400° C.

To carry out the process of the present invention, it can be advantageous to preheat the streams of the reactants prior to mixing, usually to from 100 to 600° C., preferably from 200 to 400° C.

The mean contact time of the reaction mixture in the process of the present invention is generally from 0.1 second to <5 seconds, preferably from >0.5 second to <3 seconds, particularly preferably from >0.6 second to <1.5 seconds. For the purposes of the present invention, the mean contact time is the time from the commencement of mixing of the starting materials to when the reaction mixture leaves the reaction zone.

In a preferred embodiment, the dimensions of the reaction zone and the flow velocities are such that turbulent flow occurs, i.e. the Reynolds number is at least 2300, preferably at least 2700, with the Reynolds number being based on the hydraulic diameter of the reaction zone. The gaseous reactants preferably pass through the reaction zone at a flow velocity of from 3 to 180 meters/second, preferably from 10 to 100 meters/second. As a result of the turbulent flow, a narrow residence time and good mixing are achieved. Measures such as the constriction described in EP-A-593 334, which is also susceptible to blockages, are not necessary.

The molar ratio of phosgene to diamine used in the process of the present invention is generally from 2:1 to 30:1, preferably from 2.5:1 to 20:1, particularly preferably from 3:1 to 15:1.

In a preferred embodiment, the reaction conditions are selected so that the reaction gas at the outlet from the reaction zone has a phosgene concentration of more than 25 mol/m$^3$, preferably from 30 to 50 mol/m$^3$. Furthermore, there is generally an inert medium concentration at the outlet from the reaction zone of more than 25 mol/m$^3$, preferably from 30 to 100 mol/m$^3$.

In a particularly preferred embodiment, the reaction conditions are selected so that the reaction gas at the outlet from the reaction zone has a phosgene concentration of more than 25 mol/m$^3$, in particular from 30 to 50 mol/m$^3$, and at the same time an inert medium concentration of more than 25 mol/m$^3$, in particular from 30 to 100 mol/m$^3$.

The temperature of the reaction volume is usually regulated via its outer surface. To build production plants having a high plant capacity, a plurality of reactor tubes can be connected in parallel.

The process of the present invention is preferably carried out in a single stage. For the purposes of the present invention, this means that mixing and reaction of the starting materials occurs in one step and in one temperature range, preferably in the abovementioned temperature range. Furthermore, the process of the present invention is preferably carried out continuously.

After the reaction, the gaseous reaction mixture is preferably scrubbed with a solvent at above 150° C. Preferred solvents are hydrocarbons which may be substituted by halogen atoms, for example chlorobenzene, dichlorobenzene and toluene. A particularly preferred solvent is monochlorobenzene. In the scrubbing step, the isocyanate is selectively transferred into the scrubbing solution. The remaining gas and the scrubbing solution obtained are then separated, preferably by means of rectification, into isocyanate(s), solvent, phosgene and hydrogen chloride. Small amounts of by-products remaining in the isocyanate(s) can be separated from the desired isocyanate(s) by means of additional rectification or by crystallization.

In a preferred embodiment, the process of the present invention is carried out in a production plant in which the phosgene holdup in the reaction zone for the reaction of amine with phosgene in the plant is less than 100 kg, preferably less than 60 kg, particularly preferably less than 40 kg. For the purposes of the present invention, the phosgene holdup in the reaction zone for the reaction of amine with phosgene is the mass of phosgene in kg present in the reaction zone for the reaction of amine with phosgene in normal operation.

The present invention provides a production plant which is suitable for carrying out the process of the present invention, i.e. a production plant for preparing aromatic diisocyanates by reaction of phosgene with diamines in the gas phase, preferably at an absolute pressure in the reaction zone in which the reaction takes place of more than 3 bar and less than 20 bar.

In a preferred embodiment, this is a production plant which produces from 50 000 to 500 000 metric tons of the desired diisocyanate per year, more preferably from 100 000 to 300 000 metric tons of diisocyanate per year and particularly preferably from 150 000 to 250 000 metric tons of diisocyanate per year.

The production plant of the present invention comprises stock facilities/reservoirs for diamine and phosgene, a mixing device, one or more reactors and a work-up apparatus and, if appropriate, a purification apparatus.

BRIEF DESCRIPTION OF DRAWING

An example of a production plant according to the present invention is depicted in FIG. 1.

Figure 1:
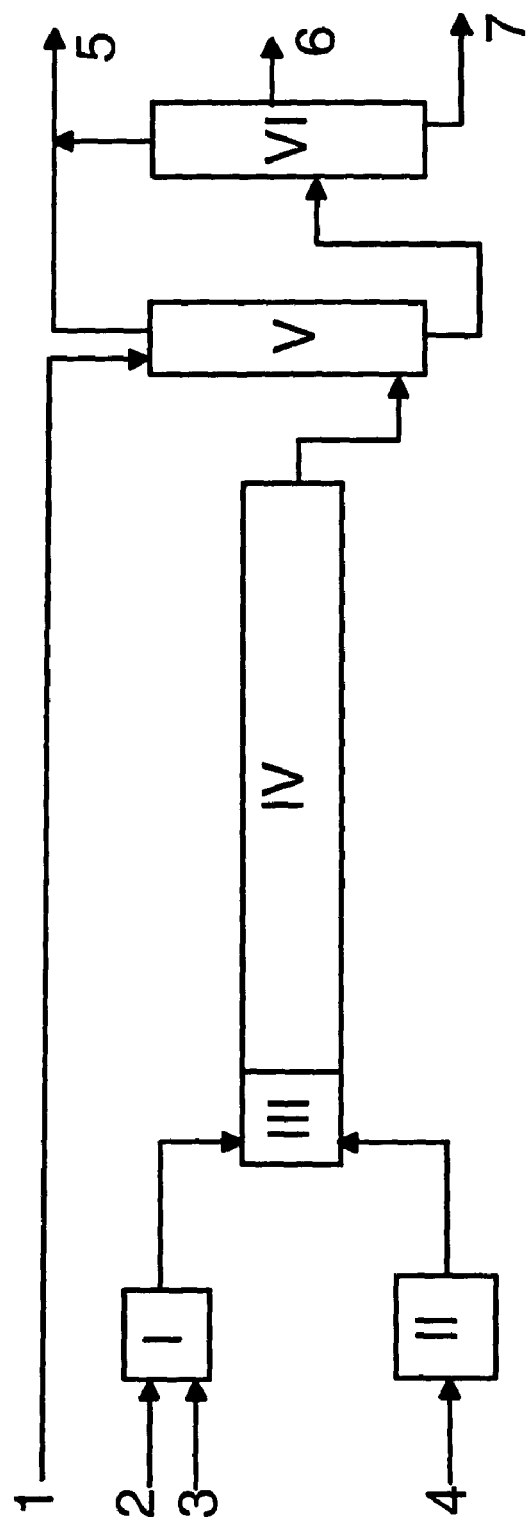
In FIG. 1 the following meanings apply:
I amine reservoir
II phosgene reservoir
III mixing unit
IV reactor
V work-up apparatus with quench
VI purification apparatus
1 solvent feed
2 amine feed
3 inert medium feed
4 phosgene feed
5 discharge of HCl and/or phosgene and/or inert medium
6 discharge of inert medium and/or solvent
7 discharge of isocyanate and/or solvent The amine reservoir, the diamine is brought into the gas phase together with an inert medium as carrier gas, for example nitrogen, and is fed into the mixing unit. Phosgene from the phosgene reservoir is likewise brought into the gas phase and introduced into the mixing unit. After mixing in the mixing unit, which can, for example, comprise a nozzle or a static mixer, the gaseous mixture of phosgene, amine and inert medium is fed into the reactor in which the reaction zone is present.

In a preferred embodiment, the reactor comprises a bundle of reactors. In one possible embodiment, the mixing unit does not have to be an independent apparatus, but instead it can be advantageous to integrate the mixing unit into the reactor. An example of an integrated unit of mixing unit and reactor is a tube reactor with flanged-on nozzles.

After the reaction mixture has been reacted in the reaction zone, it goes to the work-up apparatus with quench. This is preferably a scrubbing tower in which the isocyanate formed is separated off from the gaseous mixture by condensation in an inert solvent while excess phosgene, hydrogen chloride and, if applicable, the inert medium pass through the work-up apparatus in gaseous form. Preferred inert solvents are hydrocarbons which may be substituted by halogen atoms, for example chlorobenzene, dichlorobenzene and toluene. The temperature of the inert solvent is preferably kept above the decomposition temperature of the carbamoyl chloride corresponding to the amine.

In the subsequent optional purification stage, the isocyanate is separated from the solvent, preferably by distillation. The removal of residual impurities such as hydrogen chloride, inert medium and/or phosgene can likewise be carried out here.

The production plant of the present invention is constructed so that the ratio of production capacity to phosgene holdup is more than 3200 [metric tons of diisocyanate per year/kilograms of phosgene], preferably more than 4000, particularly preferably more than 5000. The upper limit to the ratio of maximum production capacity to phosgene holdup is generally not restricted, but a value of 20 000, preferably 10 000, has been found to be appropriate.

The invention is illustrated by the following examples:

EXAMPLE 1

A gas stream which consisted of 74 percent by mass of monochlorobenzene and 26 percent by mass of toluenediamine and had been heated to 320° C. and had a mass flow rate of 30 g/min was mixed in a mixing nozzle with a phosgene stream which had been preheated to 300° C. and had a mass flow rate of 64 g/min and the mixture was reacted at a pressure of 10 bar in a 2 meter long flow tube having an internal diameter of 8 mm. The wall of the flow tube was maintained at 380° C. The mixture leaving the flow tube had a temperature of 384° C. and was quenched in monochlorobenzene at 160° C. to scrub the isocyanate formed from the gas phase. After residual phosgene from the quench phase had been separated off by distillation, the sample was analyzed by gas chromatography. The tolylene diisocyanate yield achieved was about 99.2%. The phosgene concentration at the outlet of the flow tube was about 90 mol/m$^3$. The monochlorobenzene concentration at the outlet from the flow tube was about 35 mol/m$^3$.

EXAMPLE 2

A gas stream which consisted of 84 percent by mass of monochlorobenzene and 16 percent by mass of methylenedi(phenylamine) and had been heated to 380° C. and had a mass flow rate of 54.4 g/min was mixed in a mixing nozzle with a phosgene stream which had been preheated to 380° C. and had a mass flow rate of 44.4 g/min and the mixture was reacted at a pressure of 5 bar in a one meter long flow tube having an internal diameter of 8 mm. The reactor wall was maintained at 380° C. The mixture leaving the flow tube had a temperature of 385° C. and was quenched in monochlorobenzene at 160° C. to scrub the isocyanate formed from the gas phase. After residual phosgene from the quench phase had been separated off by distillation, the sample was analyzed by gas chromatography. The yield of methylenedi(phenyl isocyanate) achieved was about 99.3%. The phosgene concentration at the outlet from the flow tube was about 33 mol/m$^3$. The monochlorobenzene concentration at the outlet from the flow tube was about 38 mol/m$^3$.

We claim:

1. A process for preparing an aromatic diisocyanate by reacting a phosgene with a diamine in the gas phase, wherein the reaction is carried out in a reaction zone in which the pressure is more than 3 bar and less than 20 bar and the temperature in the reaction zone is from more than 200° C. to less than 600° C.

2. A process as claimed in claim 1, wherein the temperature in the reaction zone is below the boiling point of said diamine under the pressure conditions prevailing in the reaction zone.

3. A process as claimed in claim 1, wherein an inert medium is fed into the reaction zone in addition to said diamine and said phosgene in such an amount that the concentration of inert medium at the outlet from the reaction zone is more than 25 mol/m$^3$.

4. A process as claimed in claim 1, wherein the concentration of said phosgene in the reaction gas at the outlet from the reaction zone is more than 25 mol/m$^3$.

5. A process as claimed in claim 1, wherein said process is carried out continuously.

6. A process as claimed in claim 1, wherein said process is carried out in a production plant wherein the phosgene holdup in the reaction zone for the reaction of said diamine with said phosgene in the plant is less then 100 kg.

7. A process as claimed in claim 1, wherein the pressure is from 3.5 bar to 15 bar.

8. A process as claimed in claim 1, wherein the pressure is from 4 bar to 12 bar.

9. A process as claimed in claim 1, wherein the pressure is from 5 bar to 12 bar.

10. A process as claimed in claim 1, wherein the phosgene and diamine reactants are fed through feed lines to a mixing device and then mixed in said device, followed by feeding the reactants to the reaction zone, and wherein the pressure in said feed lines is from 20 to 1000 mbar higher than the pressure in the reaction zone.

11. A process as claimed in claim 10, wherein the pressure in said feed lines is from 30 to 200 mbar higher than the pressure in the reaction zone.

12. A process as claimed in claim 1, wherein products leaving the reaction zone are fed to a work-up apparatus having a pressure that is from 50 to 500 mbar lower than the pressure in the reaction zone.

13. A process as claimed in claim 12, wherein the pressure in said work-up apparatus is from 80 to 150 mbar lower than the pressure in the reaction zone.

* * * * *